United States Patent
Trajkovich et al.

(10) Patent No.: US 7,910,171 B2
(45) Date of Patent: Mar. 22, 2011

(54) METHOD OF MAKING ANTIBIOTIC LAMINATING FILM

(76) Inventors: Anthony Trajkovich, Fontana, WI (US);
Lisa Trajkovich, Crystal Lake, IL (US);
Don Woodrich, Delavan, WI (US)

( * ) Notice: Subject to any disclaimer, the term of this patent is extended or adjusted under 35 U.S.C. 154(b) by 0 days.

(21) Appl. No.: 12/480,237

(22) Filed: Jun. 8, 2009

(65) Prior Publication Data

US 2009/0243157 A1   Oct. 1, 2009

(51) Int. Cl.
*B05D 5/00* (2006.01)
*B05D 7/02* (2006.01)
*B05D 3/02* (2006.01)
*B05D 3/06* (2006.01)

(52) U.S. Cl. .............. 427/407.1; 427/535; 427/384; 427/428.06

(58) Field of Classification Search ............ 427/535, 427/384, 407.1, 428.06
See application file for complete search history.

(56) References Cited

U.S. PATENT DOCUMENTS

| | | | |
|---|---|---|---|
| 4,595,611 A | 6/1986 | Quick et al. | |
| 4,906,464 A | 3/1990 | Yamamoto et al. | |
| 4,911,898 A | 3/1990 | Hagiwara et al. | |
| 4,938,955 A | 7/1990 | Niira et al. | |
| 4,938,958 A | 7/1990 | Niira et al. | |
| 5,009,898 A | 4/1991 | Sakuma et al. | |
| 5,296,238 A | 3/1994 | Sugiura et al. | |
| 5,405,644 A | 4/1995 | Ohsumi et al. | |
| 5,441,717 A | 8/1995 | Ohsumi et al. | |
| 5,556,699 A | 9/1996 | Niira et al. | |
| 5,603,997 A | 2/1997 | Lindgren et al. | |
| 6,150,004 A | 11/2000 | Oikawa et al. | |
| 6,153,298 A | 11/2000 | Joson | |
| 6,231,953 B1 | 5/2001 | Mossbrook et al. | |
| 6,248,342 B1 | 6/2001 | Trogolo et al. | |
| 6,264,936 B1 | 7/2001 | Sawan | |
| 6,635,077 B2 | 10/2003 | Grissmayer et al. | |
| 2002/0051754 A1 | 5/2002 | Schroeder et al. | |
| 2003/0091767 A1* | 5/2003 | Podhajny | 428/35.7 |
| 2004/0156918 A1 | 8/2004 | Podhajny | |
| 2005/0019533 A1* | 1/2005 | Mossbrook et al. | 428/204 |

* cited by examiner

*Primary Examiner* — William Phillip Fletcher, III
(74) *Attorney, Agent, or Firm* — Boyle Fredrickson, S.C.

(57) ABSTRACT

An antibiotic film comprised of a base adhesive layer of Ethylene Vinyl Acetate (EVA), a second layer of Polyethylene Terephthalate (PET), and a final layer of an antibiotic, preferably a zeolite contained in a water-based acrylic coating. The antibiotic laminating film is formed by passing a base film layer with water based zeolite and acrylic dispersion coated thereon through an oven to remove all water from the dispersion. The film is then wound into a roll until it is ready for extrusion coating with a thermal adhesive. After extrusion coating, the plain side of the film is corona treated and primed to promote adhesion. The thermal adhesive is then extruded onto the primer side of the film layer and cooled. The adhesive side of the film is then cooled.

11 Claims, 4 Drawing Sheets

METHOD OF MAKING ANTIBIOTIC LAMINATING FILM

CROSS REFERENCE TO RELATED APPLICATIONS

This application claims priority from U.S. NonProvisional patent application Ser. No. 10/958,888, filed on Oct. 5, 2004, the entirety of which is expressly incorporated by reference herein.

BACKGROUND OF THE INVENTION

1. Field of the Invention

The present invention relates in general to the field of laminating films. More particularly, the present invention relates to a film having antibiotic and/or biostatic properties. Specifically, a preferred embodiment of the present invention relates to a laminating film having a first layer, a second layer, and a third layer incorporating properties to neutralize and/or destroy a variety of harmful organisms including bacteria, fungus, yeast, and viruses.

2. Discussion of the Related Art

As is known to those skilled in the art, germs and other infectious agents are everywhere. In public places, such as restaurants, the number of bacteria is often very large on items used and handled by employees and customers alike. For example, menus, placemats, recipe sheets, countertops, etc. contain thousands of potentially harmful microbes. The same is true for frequently used and handled items in other public places such as hospitals and grocery stores.

Various antibiotic compounds exist which may be used to combat some of these harmful microbes. For example, "ceramics" are commonly used to prevent bacterial growth. The "ceramics" employed in the present invention include zeolites, hydroxyapatite, zirconium phosphates or other ion-exchange ceramics. The use of Hydroxyapatite particles is described, e.g., in U.S. Pat. No. 5,009,898. Zirconium phosphates containing antibiotic metals are described, e.g., in U.S. Pat. Nos. 5,296,238; 5,441,717; and 5,405,644. Copper or Zinc zeolites are used, while silver zeolites are also popular for such application, as described in U.S. Pat. No. 6,248,342. Zeolites are preferred, and are described more fully in the preferred embodiments referred to below.

Zeolites are three-dimensional, microporous, crystalline solids with well-defined structures that contain aluminum, silicon, and oxygen in their regular framework; cations and water are located in void spaces in the pores. The silicon and aluminum atoms are tetrahedrally coordinated with each other through shared oxygen atoms. While zeolites are natural minerals, most zeolites used commercially are produced synthetically. Such antibiotic zeolite particles are well-known and can be prepared for use in the present invention using known methods. These include the antibiotic zeolites disclosed, for example, in U.S. Pat. Nos. 4,938,958 and 4,911,898. Because of their regular and reproducible structure, zeolites behave in a predictable fashion.

In the presence of moisture, the zeolite acts as an ion pump providing the controlled time release of silver ions into the environment in exchange for sodium ions from the environment. This controlled release provides continuous antibiotic protection for the product. As humidity increases and the environment becomes ideal for bacteria growth, more ions are released.

Laminated materials are commonly found throughout numerous industries. A layer of laminate provides readily used and handled materials, such as paper goods used in for example, menus or medical documents, with an outer defense layer. The laminate layer provides a coating that allows the underlying paper to be reused and recirculated while resisting the detrimental physical effects of repeated use. Use of a laminate results in a material that is resistant to tears, spills and other common detrimental effects such as scratching, fading and smudging. The most desirable laminates have sufficient clarity to provide ease of viewing the underlying printed material and are resistant to scuffing.

Thermal lamination is considered by many in the graphic arts community to be the finish of choice. With its attractive look and luxurious feel, a thermal laminated product communicates quality and creates a favorable impression with the consuming public. Thermal laminating materials (hereinafter thermolaminates) and methods are known for protecting printed substrates by adhering a protective thermoplastic polymer cover film or sheet to one or both of the major surfaces of a printed substrate. There are a wide variety of laminates to choose from, i.e., clear, delustered, satin finish, and glueable-stampable, to name but a few. See U.S. Pat. No. 6,153,298.

While known laminates provide a barrier against physical deterioration, they do little if anything to prevent the spread of harmful microbes on the surface of the laminate. Due to the widespread use of laminated materials in environments prone to bacteria, such as grocery stores and restaurants, it is desirable to have a laminating film that has antibiotic properties to resist the spread of bacterial and other unwanted microbial contaminants in addition to providing the known physical advantages.

Despite the desirability of providing such an antibiotic laminating film, previous attempts at providing such a film have proven unsatisfactory for the majority of the graphic arts industry. To date, an obvious need exists for a laminating film that provides a durable, transparent outer covering and additionally prevents the growth of microbial contaminants on the surface of the laminated material. An antibiotic and/or biostatic thermal lamination would add value to a wide range of printed materials such as library book covers, magazines, specialty packaging, posters, photographs, maps, and menus to name but a few.

SUMMARY AND OBJECTS OF THE INVENTION

In view of the foregoing, it is one object of the present invention to provide a laminating film having antibiotic and/or biostatic properties. It is another object of the present invention to provide a laminating film that neutralizes or destroys a variety of harmful microbial organisms. It is another object of the invention to provide an antibiotic laminating film that provides a sufficient physical barrier, maintains desired clarity, and is resistant to scuffing. It is another object of the present invention to provide an antibiotic laminating film that provides a satisfactory finished look as compared to prior art laminating films. Yet another object of the invention is to provide a process that can be used to relatively inexpensively manufacture an antibiotic laminating film. Still another object of the invention is to provide an antibiotic laminating film which can satisfactorily laminate high quality and high clarity graphics yet is economical to manufacture and easy to install on existing equipment.

Another object of the invention is to provide a method of manufacturing a laminating film that is predictable and reproducible, thereby decreasing variance and operating costs. Still another object of the invention is to provide a method that has one or more of the characteristics discussed above but which is relatively easy to setup.

Consistent with the foregoing objects, and in accordance with the invention as embodied and broadly described herein, an antimicrobial laminating film, an antimicrobial laminate, an antibiotic material, and a method of producing germ resistant advertisements are disclosed in suitable detail to enable one of ordinary skill in the art to make and use the invention.

By way of summary, the present invention is generally directed to a laminating film having antibiotic and/or biostatic properties to be used in a wide variety of goods and applications, and also to a method for making such a laminating film. In one embodiment, the invention is an item consisting of three layers: an adhesive ethylene vinyl acetate layer, a second PET layer, and a third antimicrobial layer. In this manner, the antimicrobial layer will be the layer of the item exposed to the atmosphere and persons in the vicinity of the item it is attached to.

These, and other, aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
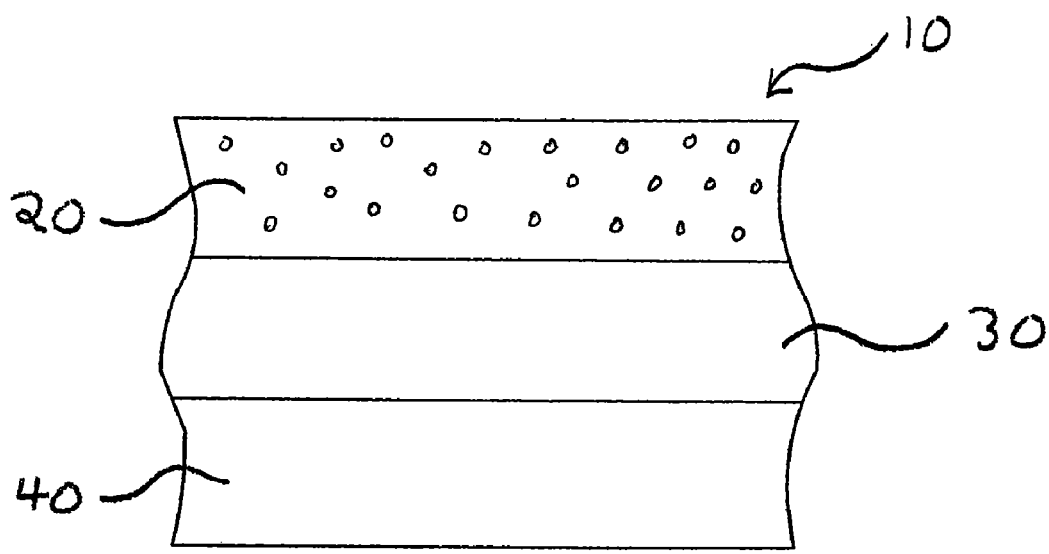
FIG. 1 illustrates a cut-away view of one embodiment according to the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DESCRIPTION OF PREFERRED EMBODIMENTS

The present invention and the various features and advantageous details thereof are explained more fully with reference to the non-limiting embodiments described in detail in the following description.

1. System Overview

As is well-known in the art, antimicrobial and antibiotic materials destroy or inhibit the development of living organisms.

The present invention is an antimicrobial and antibiotic laminating film made up of a first layer which acts as an adhesive or thermal laminate; a second layer that is parallel and adhered to the first layer, and a third or antibiotic/antimicrobial (AM) layer on top of the second layer. The antimicrobial layer preferably is an acrylic water-based emulsion and an antibiotic/antimicrobial agent. The agent is preferably a silver ion zeolite sold by AgION™ Technologies, Inc. The particles of agent are preferably less than 6 microns in size. This AM layer then is about 6 micron in thickness and is preferably transparent. Other valuable features of the laminating are its scuff resistance and its high luster look. In other embodiments, another type of solvent acrylic may be used. In another, the AM layer may be made with a silicon. The AM particles, other coatings, and emulsion are preferably applied to the film by at least one of the following: spray coating and rotogravure coating.

In one embodiment, the AM layer is comprised of an antimicrobial agent mixed with acrylic emulsion and water and suspended therein. The antimicrobial agent is suspended in acrylic coating which has been preferably baked onto the middle layer in an oven. An ultraviolet light resistant material may be incorporated into the acrylic to prevent breaking of the film and the antimicrobial material upon exposure to certain types of light waves.

The film can be attached to other materials using a thermal laminator machine. In such applications, the film is preferably a thermal laminating film. The film can also be used with solvent and water based adhesive laminations, gravure coatings and solventless adhesive laminations.

According to another embodiment of the invention, the preferred size and make up of the zeolite water-based dispersion is as follows: an acrylic, and zeolite particles that include particles having active ions and a particle size of about 6 microns, a pore size of below 3 Angstroms, and comprise from about 0.5% to about 10% by weight of the dispersion.

In one preferred embodiment the present invention, there is also a biostatic coating for reducing and preventing bacterial or microbial adhesion. This coating thereby reduces the probability of microbial and bacterial infection. The coating maybe formed from a composition containing (a) a hydrophilic polymer possessing a functional group which reacts with and covalently bonds to an amine, thiol, carboxyl, or hydroxyl active group of antimicrobial agents; (b) an antimicrobial agent which covalently bonds to the hydrophilic polymer; (c) a compatible polymer; (d) a solvent; and (e) optionally at least one additive. The solvent in the composition is then evaporated, and thereby leaving behind a biostatic coating.

In one embodiment, a new and improved method for making a thermal laminate assembly is provided comprising the steps of making a dispersion of a zeolite in a water based acrylic coating and applying the coating to a second layer. The second layer being a base film which is corona treated and then passed through an oven with sufficient temperature to thoroughly dry the water from the dispersion. After drying, the film with dried coating is wound into a roll. The roll is then extrusion coated with a thermal adhesive, i.e., the plain side of the base film is corona treated and coated with a primer to promote adhesion of the adhesive to the base film. The primer is dried, and the adhesive is extruded on to the primer side. After the adhesive is applied the film, it is then cooled. The adhesive side of the film is then corona treated to promote adhesion to the article to be laminated. The film is wound onto a roll for later slitting to the required size.

This process is advantageous because the antimicrobial properties can be added to laminating films at relatively low cost. There is no longer a need to blend antimicrobial zeolite into the base film, which is expensive and not very practical for the quantities usually required. In addition, some coatings that are commercially available for packaging films do not posses the required properties for a thermal laminate. Applications for the inventive film include the following: a menu laminate; food service counter mats; drink dispensing button covers; posters; medical documentation; product displays; shopping cart placards, emergency manuals; materials having decorative films; placemats; and decontamination gear.

The inventive material can be further combined with the following: high clarity films, curl resistant films, printable, glueable, clear, metalized or holographic products, colored films, a variety of textured films, and a transparent laminating film specifically designed to provide protection and enhancement to printed products.

2. Detailed Description of Preferred Embodiments

Specific embodiments of the present invention will now be further described by the following, non-limiting examples which will serve to illustrate various features of significance. The examples are intended merely to facilitate an understanding of ways in which the present invention may be practiced and to further enable those of skill in the art to practice the present invention. Accordingly, the examples should not be construed as limiting the scope of the present invention.

Referring now to FIG. 1, a new and improved thermal laminating film in accordance with an embodiment of the invention generally referred to by reference numeral 10, is shown. The thermal laminating film 10 comprises a first layer 40, preferably of ethylene vinyl acetate (EVA), to act as an adhesive, a second or finish layer 30, preferably of polyester, e.g., polyethylene terephthalate (PET) adhered to the first layer 40, and a third or antibiotic, biostatic, and/or antimicrobial (AM) layer 20 covering the second PET layer 30. The antibiotic used in the AM layer 20 is preferably a zeolite such as the commercially available AJ10D from AgION™ Technologies, Inc. of Wakefield, Mass., contained in a water based acrylic coating such as the commercially available acrylic from Grant Industries.

It is understood, however, that the antibiotic could be comprised of other elements. Moreover, for example, in antibiotic zeolite particles for use in the present invention, ion-exchangeable ions present in zeolite, such as sodium ions, calcium ions, potassium ions and iron ions are preferably partially replaced with ammonium and antibiotic metal ions. Such ions may co-exist in the antibiotic zeolite particle since they do not prevent the bacteriocidal effect. In addition to silver, copper, silicon, and zinc, the antibiotic metal ions may include ions of mercury, tin, lead, bismuth, cadmium, chromium, thallium, and gold. Any of these antibiotic metal ions can be used by themselves or in a mixture.

The antibiotic properties of the formulations of the invention should be sufficient enough to prevent the growth of a variety of bacteria, eumycetes and yeast, including:
Listeria,
Bacillus cereus var mycoides,
Escherichia coli,
Pseudomonas aeruginosa,
Salmonella typhimurium,
Staphylococcus aureus,
Streptococcus faecalis,
Aspergillus niger,
Aureobasiduim pullulans,
Chaetomium globosum,
Gliocladium virens,
Penicillum funiculosum,
Candida albicans,
Saccharomyces cerevisiae.

Figure 2:
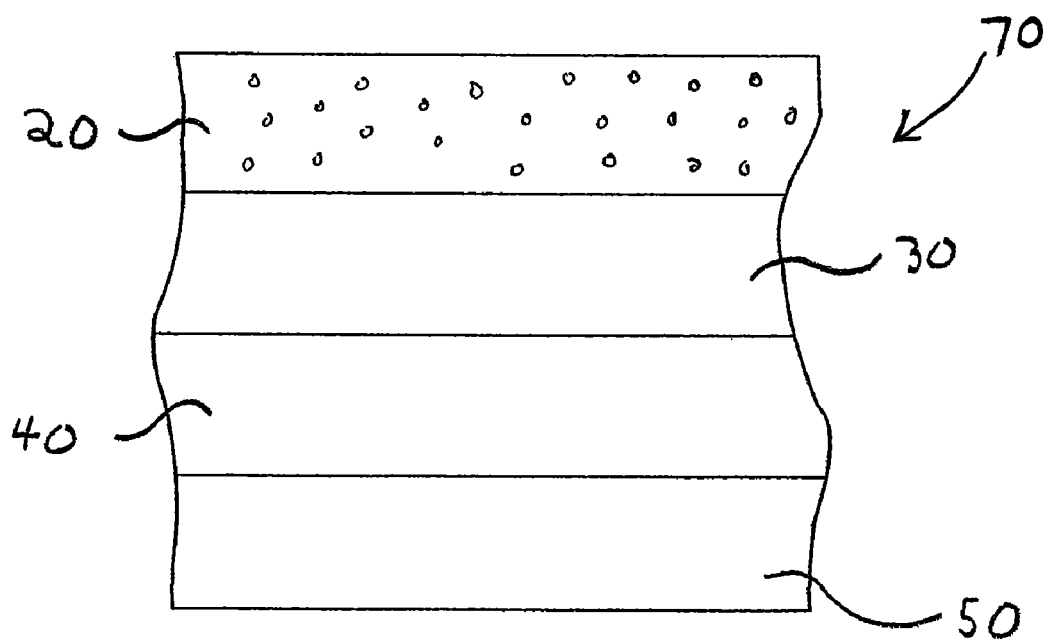
FIG. 2 is a cross-sectional view of a new and improved thermal laminating film attached to a surface in accordance with the present invention.
Figure 3:
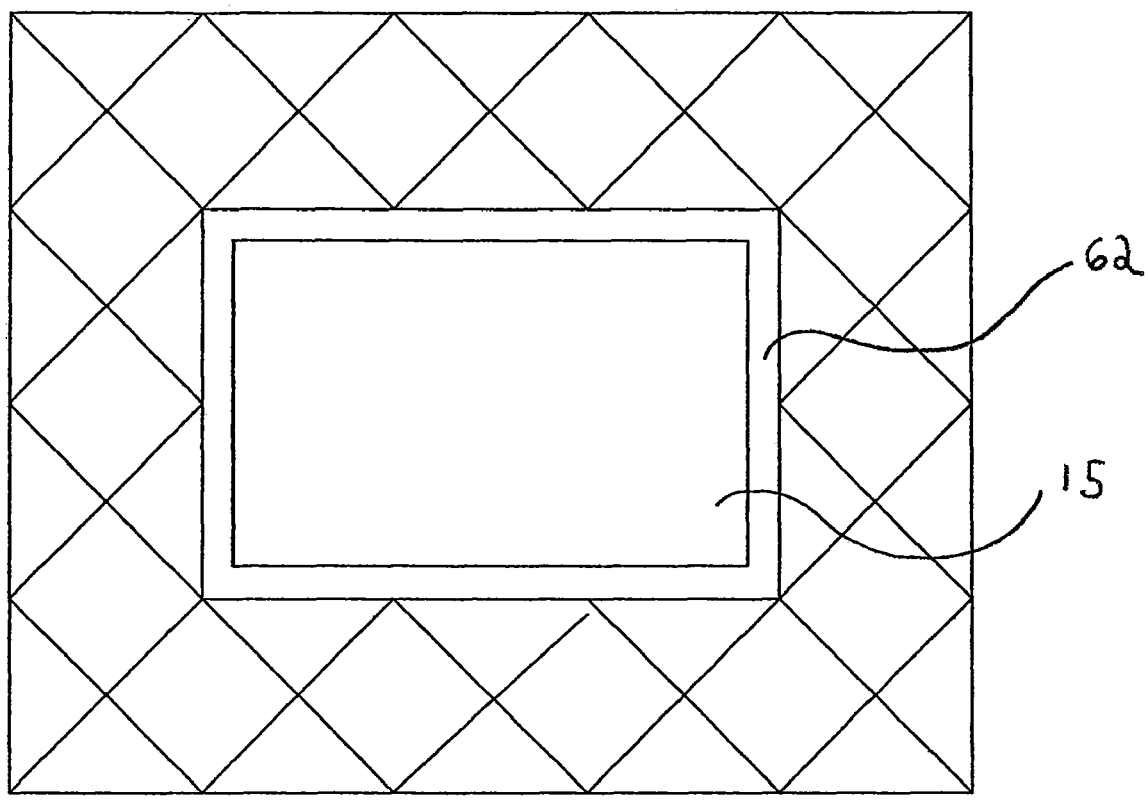
FIG. 3 illustrates one embodiment of the present invention in use on an advertising placard of a shopping cart.
Figure 4:
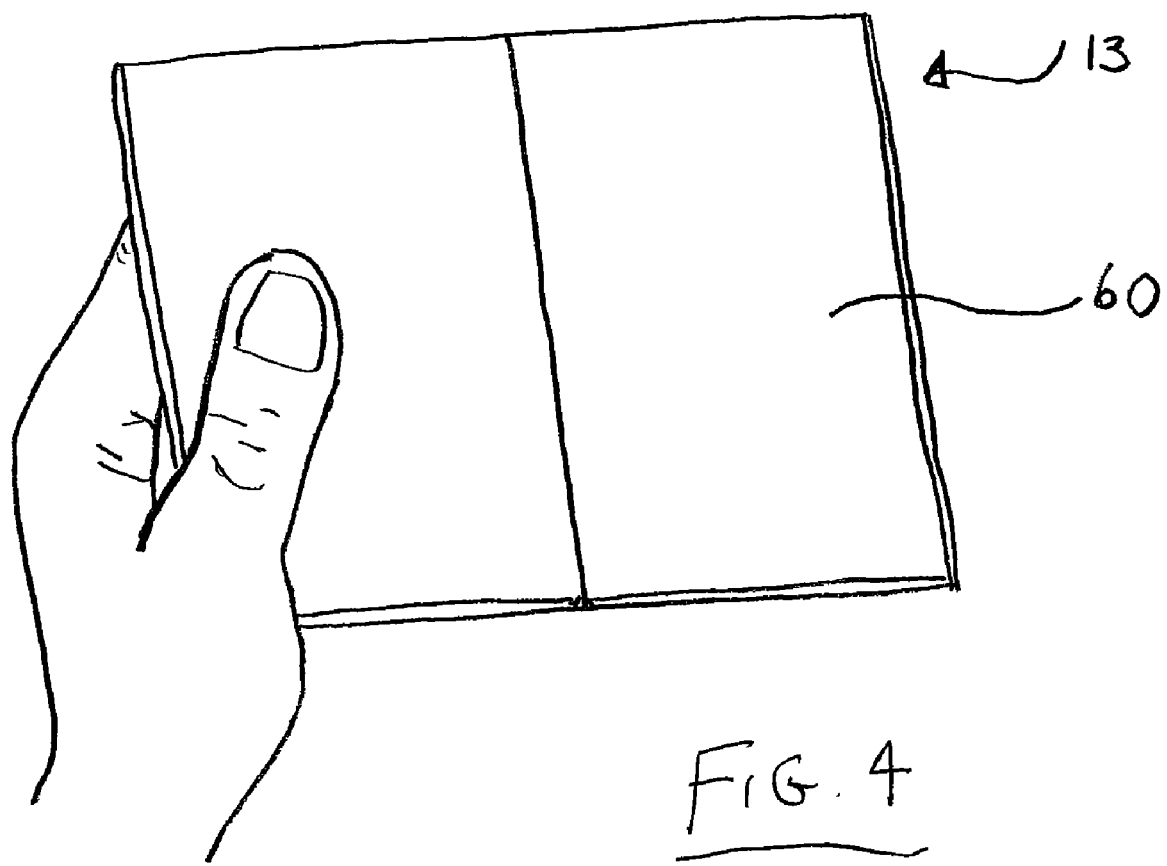
FIG. 4 illustrates one embodiment of the present invention in use on a menu.
Figure 5:
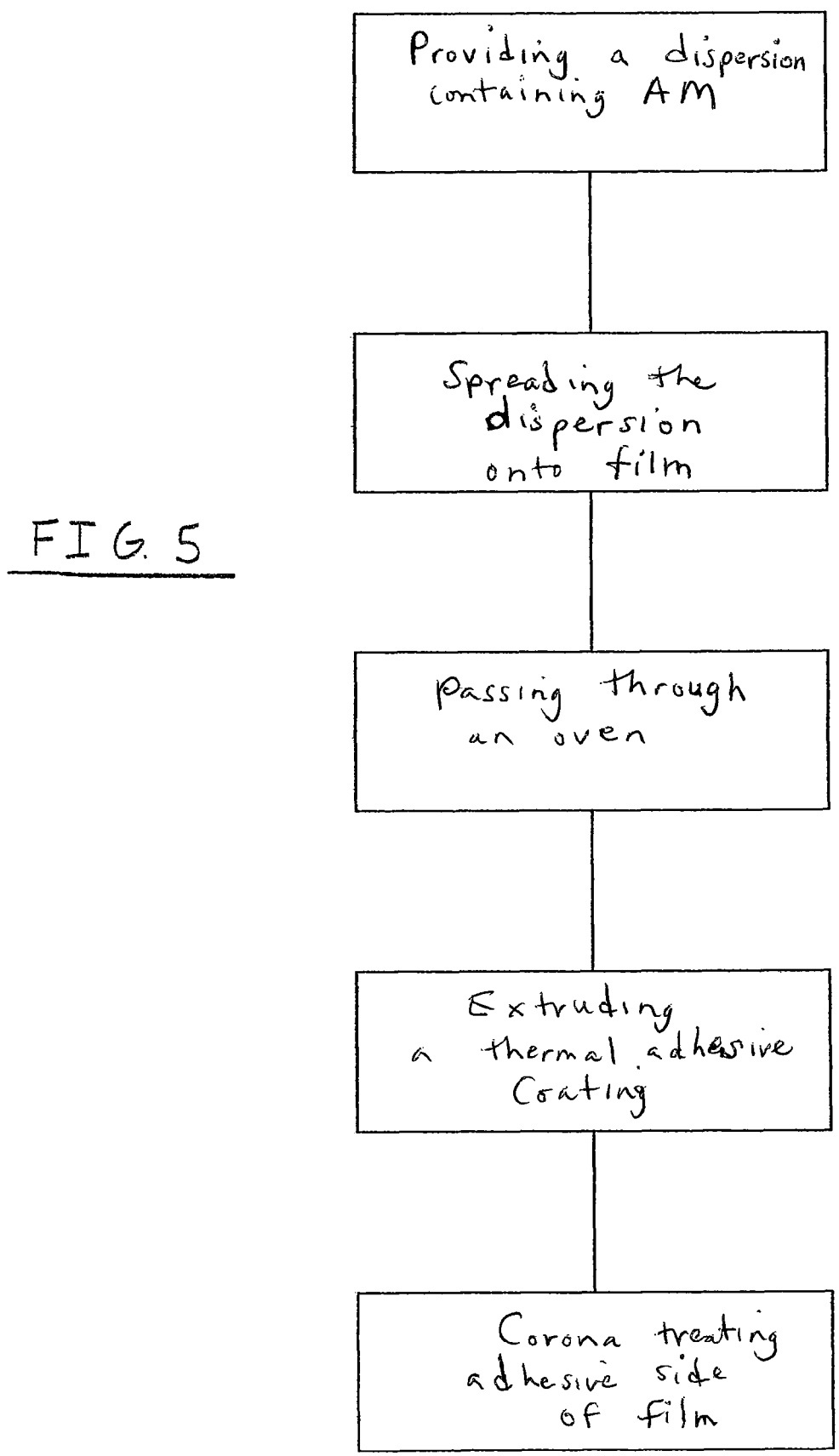
FIG. 5 illustrates a flow chart of the preferred method of manufacture of the antibiotic laminating film.

As illustrated in FIG. 2, the thermal laminating film 10 may be attached to a surface 50, such as a printed item, by means of the adhesive nature of the first layer 40. Although the film may have a variety of thicknesses, it is preferred that the total film thickness range from about 15 to 300 microns.

In accordance with this embodiment, the adhesive first layer 40 comprises from about 40 to about 90% by weight of an ethylene vinyl acetate copolymer containing from about 0.1 to about 40% by weight of vinyl acetate units. The first layer may also include an amount of an anti-blocking agent which is effective at preventing the thermal laminating film 10 from sticking to roller surfaces, from fusing along an edge portion thereof, or from blocking upon slitting when the thermal laminating film 10 is wound on a roll. The first layer may also include an ultraviolet absorber and may comprise any other additives conventionally used by those skilled in this art. The thermal laminating or first layer 40 may have a thickness of from about 0.0003 to about 0.010 inches.

The second layer 30 may comprise any suitable thermoplastic polymer sheet material useful for thermal lamination applications. It the preferred embodiment, the second layer 30 has a thickness of about 0.0004 to about 0.010 inches. Preferably, the thermoplastic polymer sheet material is translucent or especially preferably transparent and possesses surface characteristics and other physical properties such as flexibility, durability, hardness, scratch resistance and the like, for protecting a printed surface to which the thermal laminating film may be laminated. Illustrative thermoplastic polymer sheet materials include polyethylene, particularly polyethylene terephthalate (PET), oriented polypropylene (OPP), non-oriented polypropylene, polyesters, polyamides (e.g., nylon), polyvinyl chloride, polycarbonates and textured film.

The antimicrobial layer 20 is preferably formed from a dispersion comprising a mixture of acrylic, water, and zeolite particles. Preferably, the particles have active ions and a particle size of about 6 microns, a pore size of below 3 Angstroms, and comprise from about 0.5% to about 10% by weight of the dispersion. Preferably, the dispersion has a viscosity between about 20 and about 1000 centipoise. In the preferred embodiment, the zeolites comprise from about 0.25% to about 3% by weight of the dispersion. The acrylic may comprise from about 15% to about 60% by weight of the dispersion. It is understood that the preferred dispersion could be applied in a variety of ways such as spray coating, rotogravure coating, or printing. Once dried, the dispersion is commonly referred to as a coating.

It is understood that the inventive thermolaminate may include other decorative features such as a high clarity film, curl resistant film, printable film, clear film, metalized film, holographic film, colored film, or textured film.

3. Method of Manufacture

In order to manufacture the antibiotic laminating film 10 of the present invention, the dispersion of the zeolite in a water based acrylic coating previously described is utilized. During a first pass, the acrylic dispersion is coated by the rotogravure process onto a second or base film layer. A base film consisting of, but not limited to, for example, PET, OPP, Nylon, is utilized. Preferably, the base film (which makes up the second layer) is corona treated, or has in line corona treating capability. The base film with coating is then passed through an oven with sufficient temperature, to thoroughly dry the water from the dispersion. After drying, the base film 30 with dried coating 20 (i.e., the third layer) is wound into a roll. The roll from the first pass is then extrusion coated with a thermal adhesive (to make up the first layer). In one preferred embodiment, the coating is accomplished by unwinding the roll from the first pass so that the adhesive is placed on the opposite side as the coating. The plain side of the base film is then corona treated, and coated with a primer to promote adhesion of the adhesive to the base film. The primer is dried, and the adhesive 40 is extruded onto the primer side. The adhesive is preferably applied in thicknesses between 0.75 and 10 mils. After the adhesive is applied the film is then cooled with a chill drum to about 100 degrees Fahrenheit. The adhesive side of the film is then corona treated to promote adhesion to the article to be laminated. The film is wound onto a roll for later slitting to the required size. Finally, additives such as an anti-blocking agent or ultraviolet absorber may be added. Known thermal lamination techniques are used to apply the inventive film 10 to a substrate. Thermal lamination is the process of combining a heated web to second webs or sheets. The process uses dry non-tacky film until it is heated. The combining station is typically comprised of two rollers. One of the rollers may be steel and internally heated and may have a polished surface. The other may be a rubber covered impression roller. A typical single-sided laminator apparatus is disclosed in U.S. Pat. No. 4,960,484.

Referring now to FIGS. 1 through 4, embodiments of a new and improved thermal laminate in accordance with the present invention is shown. The thermal laminate generally comprises a printed substrate including a substrate layer having a surface 50 and printed ink disposed imagewise on surface 50. The new and improved antibiotic thermal laminating film 10 is thermally laminated onto the printed surface 50 of the substrate so that the second PET layer 30 and the first layer or thermal laminating layer 40 are intimately contacted and bonded to the printed surface 50 of the substrate.

In accordance with the present invention, the new and improved thermal laminating film 10 is capable of being directly used in conventional thermal laminating equipment to satisfactorily thermally laminate the new and improved thermal lamination film 10 onto printed sheets or substrates for use with menus, medical documents, advertisements, etc. The thermal laminate 10 may be prepared using commercially available equipment such as those available from Protect-All, Inc. of Darian, Wis.

Using known laminating equipment, a printed substrate to be laminated is fed into the laminating equipment to a positive stop in a thermal lamination station. Thereafter, the thermal laminating film 10 is moved relative to the printed substrate and positioned in the laminating station so that the thermal laminating film 10 is disposed in overlying registering relation to the printed substrate and so that the first layer 40 is disposed in face to face contact with the printed surface 50 of the substrate to form a pre-assembly. Thereafter, the pre-assembly is subjected to conditions of elevated temperature and pressure by means of applying a heated roller, along the entire length of the pre-assembly. Typical thermal lamination temperatures are from about 210 degrees to 285 degrees Fahrenheit. The heated rollers are usually heated by water. The inwardly directed pressures provided by rollers, compressing the pre-assembly, typically range from about 50 to about 70 pounds per lineal inch. When pre-assembly is passed through the heated rollers, the thermal laminating layer 40 rapidly melts and effectively bonds the thermoplastic polymer film 30 to the printed surface 50 of the substrate creating a thermo laminated material 70.

In one method, the acrylic dispersion may later be coated, for example, onto the surface of a printed item or an advertisement to create a germ resistant surface, and dried to form a coating layer having an exposed surface containing zeolites. Preferably, the surface is coated by the dispersion at a rate of about 0.1 lbs./3000 ft. square to 1 lbs./3000 ft. square and the coating layer has a thickness of from about 0.7 microns to about 7 microns.

In the preferred embodiment, the advertisement may include materials such as, cellophanes, vinyl chlorides, vinyl chloride copolymers, cellulose acetate films, vinylidene chlorides, vinylidene chloride copolymers, ethyl cellulose, aluminum foils, methyl cellulose, laminates, polyesters, papers, polyethylenes, paperboards, polypropylenes, glassines, polystyrenes, nylons and combinations thereof.

The present invention has a plurality of additional uses. In one preferred embodiment illustrated in FIG. 4, the printed item having an antimicrobial film 15 may be a menu 60. In another preferred embodiment illustrated in FIG. 3, the printed item having an antimicrobial film 15 may be an advertisement or announcement on a shopping cart placard 62.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

For example, the invention discloses in one embodiment an antibiotic zeolite. However, a contact antibiotic such as quaternary ammonium and phosphonium salts covalently bound to a polymeric material that may be suitable in a variety of applications. Alternatively, the use of an inorganic antibiotic metal containing composition is contemplated, such as, an antibiotic metal salt. Such salts include silver acetate, silver benzoate, silver carbonate, silver iodate, silver iodide, silver lactate, silver laurate, silver nitrate, silver oxide, silver palmitate, silver protein, and silver sulfadiazine. Silver nitrate is preferred.

Moreover, the effectiveness of the antibiotic zeolite particles can be prolonged if the particles are separated from the deactivating ingredients of the formulation by a barrier composition or microencapsulation. Such a barrier prevents contact of the zeolite particles with the deactivating agents. Examples of barrier compositions that can be used include polyacrylic acid, sorbitol, polysorbate, starch, agar, carboxymethyl cellulose, PEG, and any suitable material, including polymeric materials, or in particular thermoplastic and thermosetting polymers. Preferably, a gelling polymer is employed as a barrier layer. Carbopol is an appropriate gelling polymer that is commonly commercially available.

Further, it is possible to employ such barrier layers in several ways. For example, the barrier layer may be employed to microencapsulate individual particles of antimicrobial zeolite. Alternately, several particles of antimicrobial zeolite may be distributed within each "drop" of a barrier material. For example, assemblages of several antibiotic zeolite particles can be coated with Carbopol. The coatings are preferably of a thickness to allow easy release of the particles, while protecting the silver in the particles from deactivating ingredients. As it has been determined that such compositions are capable of exhibiting a long shelf life, it is also possible to microencapsulate individual antibiotic particles, e.g., in starch or agar, and to then incorporate the microencapsulated particles into another barrier layer, e.g., Carbopol. Further, where the inorganic antibiotic metal containing composition is a silver salt, the barrier layer can isolate the silver salt from inactivating ingredients.

Where antibiotic zeolite particles are microencapsulated, conventional microencapsulation compositions and techniques are employed. For example, it is possible to coat individual particles with starch, agar, or polymer using conventional methods such as spray drying, fluidized bed coating, electrostatic deposition, centrifugal extrusion, rotational suspension separation, polymerization at a phase boundary, pressure extrusion, or spraying into a solvent bath. Chemical processes of microencapsulation are also possible, such as complex coacervation, polymer-polymer incompatibility methods, interfacial polymerization, in-situ polymerization, in-liquid drying, thermal or ionic gelation, and desolvation in liquid media. Microencapsulation techniques usable to coat the antibiotic zeolites are well-known in the pharmaceutical industry, and include, for example, methods described in U.S. Pat. Nos. 5,503,851 and 5,393,533 among many other known methods.

Further, one or more surfactants can also be added to the composition, in particular to aqueous slurries of antibiotic zeolite employed, to prevent aggregation.

Finally, while acrylic is the preferred type of dispersion, the dispersion may include at least one of the following: polyamides, polyvinyl chloride, methyl methacrylates, polyurethanes, ethyl cellulose, polyvinylbutyral, polyketones, nitrocelluloses, sulfonated polyesters, shellacs, polyurethanes, maleics.

It is intended that the appended claims cover all such additions, modifications and rearrangements. Expedient embodiments of the present invention are differentiated by the appended claims.

What is claimed is:

1. A method of generating an antibiotic laminating film comprising:
   providing a dispersion of a zeolite in a water based acrylic coating;
   spreading the dispersion onto a base film layer;
   passing the base film layer with the dispersion coated thereon through an oven to remove all water from the dispersion;
   winding the dried base film layer into a roll;
   extrusion coating the roll the base film layer with a thermal adhesive;
   corona treating a plain side of the film layer;
   priming the plain side of the film layer to promote adhesion;
   drying the primer;
   extruding a first adhesive onto the primer side of the film layer;
   cooling the film layer and the first adhesive to a temperature of about 100 degrees Fahrenheit; and
   corona treating the first adhesive side of the film.

2. The method of claim 1, wherein the spreading step comprises coating the acrylic dispersion by a gravure process.

3. The method of claim 1, wherein the base film layer comprises at least one of the following: PET, OPP, nylon, and textured film.

4. The method of claim 3, further comprising adding at least one of: an anti-blocking agent and an ultraviolet absorber.

5. A method of producing a germ resistant advertisement having graphics and at least one polymer surface, the method comprising the steps of:
   a. providing a water-based dispersion comprising an acrylic and zeolite particles, wherein the zeolite particles have active ions and a particle size of about 6 microns, a pore size of below 3 Angstroms, and comprise from about 0.5% to about 10% by weight of the dispersion;
   b. coating the dispersion onto a surface of an advertisement to create a germ resistant surface, wherein the advertisement is made from the group consisting of cellophanes, vinyl chlorides, vinyl chloride copolymers, cellulose acetate films, vinylidene chlorides, vinylidene chloride copolymers, ethyl cellulose, aluminum foils, methyl cellulose, laminates, polyesters, papers, polyethylenes, paperboards, polypropylenes, glassines, polystyrenes, nylons and combinations thereof and; and
   c. drying the dispersion to form a coating layer having an exposed surface containing the zeolite particles, wherein the advertisement further includes a thermal laminating film comprising:
   a base layer of a thermoplastic polymer sheet material having a surface, and a unitary thermal laminating layer disposed on the surface, the unitary thermal laminating layer comprising from about 40% to about 90% by weight of an ethylene vinyl acetate copolymer containing from about 0.1% to about 40% by weight of vinyl acetate units, and
   an amount of an anti-blocking agent effective, when the thermal laminating film is wound on a roll, to prevent the thermal laminating film from sticking to roller surfaces.

6. The method of claim 5, wherein the surface is coated by the dispersion at a rate of about 0.1 lbs./3000 ft, square to 1 lbs./3000 ft, square.

7. The method of claim 5, wherein the coating layer has a thickness of from about 0.7 microns to about 7 microns.

8. The method of claim 5, wherein, the dispersion has a viscosity between about 20 centipose and about 1000 centipoise.

9. The method of claim 5, wherein the zeolite particles comprise from about 0.25% to about 3% by weight of the dispersion.

10. The method of claim 5, wherein the acrylic particles preferably comprise from about 15% to about 60% by weight of the dispersion.

11. The method of claim 5 wherein the dispersion is coated using rotogravure printing.

* * * * *